(12) United States Patent
Wernet et al.

(10) Patent No.: US 9,983,552 B2
(45) Date of Patent: May 29, 2018

(54) SYSTEM OF SERVICING DEVICE AND FIELD DEVICE AND METHOD FOR COMMUNICATION WITH A FIELD DEVICE

(71) Applicant: Endress + Hauser GmbH + Co. KG, Maulburg (DE)

(72) Inventors: Armin Wernet, Rheinfelden (DE); Kag Uppenkamp, Wehr (DE)

(73) Assignee: ENDRESS + HAUSER GMBH + CO. KG, Maulburg (DE)

( * ) Notice: Subject to any disclaimer, the term of this patent is extended or adjusted under 35 U.S.C. 154(b) by 793 days.

(21) Appl. No.: 14/359,592

(22) PCT Filed: Oct. 23, 2012

(86) PCT No.: PCT/EP2012/070935
§ 371 (c)(1),
(2) Date: May 21, 2014

(87) PCT Pub. No.: WO2013/079260
PCT Pub. Date: Jun. 6, 2013

(65) Prior Publication Data
US 2014/0339919 A1 Nov. 20, 2014

(30) Foreign Application Priority Data
Nov. 28, 2011 (DE) .................. 10 2011 087 230

(51) Int. Cl.
*G05B 11/01* (2006.01)
*H01H 51/00* (2006.01)
(Continued)

(52) U.S. Cl.
CPC ............. *G05B 11/01* (2013.01); *G01D 21/00* (2013.01); *G01F 23/2967* (2013.01);
(Continued)

(58) Field of Classification Search
USPC ........................................... 307/116
See application file for complete search history.

(56) References Cited

U.S. PATENT DOCUMENTS 7,336,068 B2 * 2/2008 Muller ................ G01D 18/008
324/202
2009/0174921 A1 7/2009 Sendo
(Continued)

FOREIGN PATENT DOCUMENTS

CN 1602413 A 3/2005
CN 1023621270 A 2/2012
(Continued)

OTHER PUBLICATIONS

German Search Report, German PTO, Munich, dated Mar. 12, 2012.
(Continued)

*Primary Examiner* — Jared Fureman
*Assistant Examiner* — Aqeel Bukhari
(74) *Attorney, Agent, or Firm* — Bacon & Thomas, PLLC

(57) ABSTRACT

A system composed of a servicing device and a field device having at least one sensor unit for determining and/or monitoring at least one process variable. At least one electronics unit, which has an evaluation unit, wherein the evaluation unit receives measurement signals from the sensor unit and evaluates such with reference to the process variable, and at least one switch element actuatable contactlessly from outside of the field device. The servicing device is embodied to modulate the switch state of the switch element for transmission of field device specific data to the electronics unit. Furthermore, a field device, a servicing device and a method for communication between field device and servicing device are claimed.

9 Claims, 2 Drawing Sheets

(51) Int. Cl.
*H04B 5/00* (2006.01)
*G01F 23/296* (2006.01)
*G01D 21/00* (2006.01)
*G01N 9/34* (2006.01)

(52) U.S. Cl.
CPC ........... *H01H 51/00* (2013.01); *H04B 5/0031* (2013.01); *H04B 5/0043* (2013.01); *G01N 9/34* (2013.01); *Y10T 307/766* (2015.04)

(56) References Cited

U.S. PATENT DOCUMENTS

2010/0237229 A1* 9/2010 Yanagisawa .......... G01J 1/4204
250/214 A
2012/0022794 A1 1/2012 Andelic
2013/0217332 A1* 8/2013 Altman .................. H04H 60/90
455/41.2

FOREIGN PATENT DOCUMENTS

| DE | 10162334 A1 | 7/2003 |
| DE | 102009007109 A1 | 8/2010 |
| EP | 0718607 A2 | 6/1996 |
| GB | 1322434 | 7/1973 |
| WO | 03052358 A1 | 6/2003 |

OTHER PUBLICATIONS

International Search Report, EPO, The Netherlands, dated Feb. 26, 2013.
English Translation of the International Preliminary Report on Patentability, WIPO, Geneva, Jun. 12, 2014.
"Modulation", from Wikipedia. Edited by Johnuniq, Nov. 2011.

* cited by examiner

SYSTEM OF SERVICING DEVICE AND FIELD DEVICE AND METHOD FOR COMMUNICATION WITH A FIELD DEVICE

TECHNICAL FIELD

The present invention relates to a system composed of a servicing device and a field device having at least one sensor unit for determining and/or monitoring at least one process variable. Furthermore, the invention relates to a field device as well as a servicing device for application in the system. Moreover, the invention relates to a method for communication with a field device. The field device is, for example, a measuring device of process automation, especially a measuring device for determining the fill level, the limit level, the density, the viscosity, or the electrical conductivity of a medium.

BACKGROUND DISCUSSION

Many field devices require parametering by the manufacturer. A possibility for this lies in the use of a manufacturing interface, which uses an existing interface, for example, a HART interface. Such an interface is, however, as a rule, no longer usable, once the field device is completely assembled, respectively potted. For the final adjustment of a pre-tailored field device, consequently, a separate interface is required. Such interfaces provide a contactless connection for parametering, for example, via radio, RFID or optical paths. The implementing of such interfaces is, however, costly, or, due to a completely closed metal field device housing, often not implementable at all.

SUMMARY OF THE INVENTION

An object of the invention is to provide a system composed of, firstly, a field device with a cost effectively implementable communication interface and, secondly, a servicing device, as well as a cost effectively implementable method for communication between field device and servicing device.

The object is achieved by a system composed of field device and servicing device, wherein the servicing device is embodied to modulate the switch state of a switch element for transmission of field device specific data to the electronics unit.

Known are field devices having an externally actuatable switch element for initiating a calibration procedure. The switch element is, for example, a reed switch. Such is actuated by a magnet, which is applied externally on the field device housing. Such a field device is described, for example, in Offenlegungsschrift, or German laid open application DE 101 62 334 A1. The present invention provides that an externally actuatable switch element is activated not only for initiating a certain function but also for implementing a communication interface.

The switch element is a contactlessly actuatable switch element. Because of this, the housing of the field device can be hermetically sealed, without having to forego accessing of the electronics unit of the field device. Preferably present is exactly one switch element. The electronics unit is embodied to receive data in the form of electrical signals, for example, electrical current pulses, via the switch element.

In a first embodiment, the switch element is actuatable from outside of the field device via a magnetic field and the servicing device produces a modulatable magnetic field. The switch element is an analog or digital, magnetic field sensitive component, preferably an analog or digital Hall sensor or a reed switch. Frequently, a reed switch is already present in a field device, for example, for initiating a calibration function or a function test. In this case, communication via a reed switch is especially cost effectively implementable, since an element present in any event is used for the communication. In contrast to reed switches known from the state of the art, the reed switch in the case of a field device of the invention serves not only as an activation switch but instead, or additionally, for data transmission. In such case, data are transmitted from the servicing device to the field device, or to the field device starting out from an external device. In the latter case, the servicing device acts as a go between, since only the servicing device is embodied to control the switch element integrated in the field device.

In an embodiment, the field device includes at least one optical display element and the electronics unit transmits data to the servicing device via the optical display element. The servicing device possesses, correspondingly, an optical sensor system for registering and processing the optical signals. The optical display element provides an optical interface in the form of a read response function. The data, which the field device transmits to the servicing device, is, for example, data relative to the configuration or the operating state of the field device, measurement parameters or other field device specific data.

The object is furthermore achieved by a field device for application in a system of the invention, wherein the field device comprises at least one sensor element for determining and/or monitoring at least one process variable, at least one electronics unit and at least one switch element actuatable contactlessly from outside of the field device, wherein the electronics unit is embodied to receive field device specific data via the switch element. The field device specific data transmitted via the switch element are, for example, parameter data or diagnostic data. The electronics unit stores the transmitted data, for example, in a memory unit, so that such are available during measuring, or effects settings corresponding to the data. If of concern is diagnostic data, the electronics unit executes a certain diagnostic function. The contactlessly actuatable switch element makes possible not only a storing of information in the field device but also a retrieving of information. For example, the field device outputs queried information via a 4-20 mA interface.

Furthermore, the object is achieved by a servicing device for application in a system of the invention, wherein the servicing device comprises at least one field producing unit for producing a modulatable magnetic field, wherein the field producing unit is embodied in such a manner that the magnetic field produced by the field producing unit modulates the switch state of the switch element of the field device. The field producing unit is preferably embodied as a coil, through which flows a controllable electrical current and which has a coil core.

In an embodiment, the servicing device includes an optical sensor system, which registers optical signals coming from the field device. The optical sensor system is preferably arranged in such a manner that it is shielded from ambient light. Preferably, the optical sensor system transduces the optical signals into electrical signals, for example, voltage signals, and provides these as output signal. Either the servicing device has an evaluation unit for evaluating the output signal of the optical sensor system or the output signal is fed to an external device, for example, a computer.

Another embodiment provides: that the servicing device has a second electronics unit and means for input of field device specific data or is connectable with a second electronics unit and means for input of field device specific data; that the second electronics unit contains a protocol for transmission of field device specific data to the field device; and that the second electronics unit controls the field producing unit in such a manner that the field producing unit produces the magnetic field corresponding to the protocol and corresponding to the data to be transmitted. Communication between the field device and the servicing device via the switch element occurs via telegrams produced according to the preselected protocol. The communication via a, in given cases present, optical interface occurs likewise according to the preselected protocol.

Furthermore, the object is achieved by a method for communication between a servicing device and a field device having at least one sensor unit, at least one electronics unit and at least one switch element actuatable contactlessly from outside of the field device, wherein for transmission of field device specific data from the servicing device to the electronics unit the switch state of the switch element is modulated. The switch element provides a serial data communication.

In an embodiment of the method, the switch state of the switch element is modulated according to a transmission protocol. For the case, in which the switch element is embodied as a magnetic field sensitive element, the transmission protocol is, in such case, so selected that predominantly the open state is present and only so often as necessarily required are pulses transmitted. The element, which produces the magnetic field, is, in the simplest case, a coil with a coil core. The embodiment wherein the switch element is kept primarily in the open state prevents that the coil core in the case of producing the magnetic field required for the data transmission becomes saturated. A suitable protocol is, for example, an IrDA protocol, such as e.g. SIR (Serial Infrared) known for transmission via infrared interfaces. The method of the invention enables a safe transmission of field device specific data to the field device. Especially, safe transmission can be assured using checksum techniques.

In an embodiment of the method, parameter data and/or diagnostic data are transmitted by means of the switch element. Parameter data comprise all data, which concern settings of the field device, for example, calibration data, parameters of furnished comparison curves for the measuring, tolerances in the case of determining the value of an output signal, device variants, or information relative to supplemental functions. Parameter data are stored by the electronics unit in a memory unit. Diagnostic data include data, which are in any manner suitable for diagnosing a defect in one or more components of the field device. The diagnosis can also refer to future behavior of the components in the context of predictive maintenance. For example, the diagnostic data cause a predetermined output signal to be produced or an LED to be activated.

An advantage of the invention in connection with fill level measuring devices is, for example, that an opportunity is created to be able subsequently to change a switching curve stored in the electronics unit of the field device, without having to disassemble the field device. In the manufacturing of the field device there results, furthermore, the advantage that a calibrating or an adjustment in the case of completely assembled field device with potted electronics unit can be performed, so that possible influences of the potting material on the determining or monitoring of the process variable can already be taken into consideration.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1:
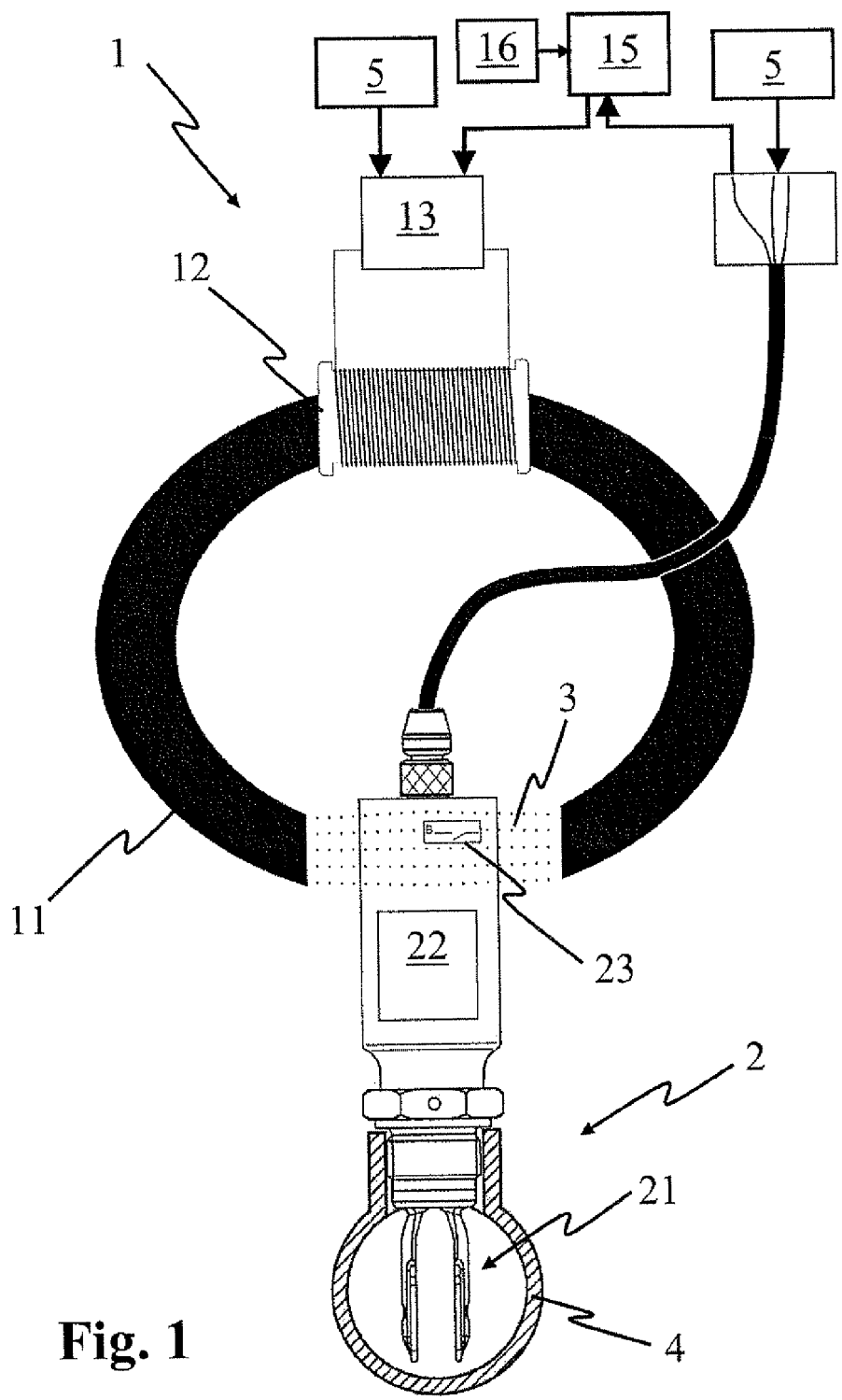
FIG. 1 is a first form of embodiment of a system composed of field device and servicing device.

FIG. 1 shows a first form of embodiment of a field device 2 with a sensor unit 21 for determining the density, the viscosity, and/or a limit level of a medium, as well as a servicing device 1 for communication with the field device 2. Furthermore, a container 4 is schematically presented, to which the field device 2 is secured.

Sensor unit 21 of the field device 2 includes an oscillatable unit in the form of a fork with paddle shaped tines. For determining whether a fill level, respectively limit-level, predetermined by the height, at which the sensor unit 21 is arranged in the container 4, has been achieved, the oscillatable unit is excited by a driving and receiving unit to execute mechanical oscillations with its resonant frequency. The driving and receiving unit, furthermore, receives the oscillations of the oscillatable unit and transduces them into an electrical signal. The driving and receiving unit is preferably one or more piezoelectric elements. The reaching of the fill level is detectable by a change of the oscillation frequency, which occurs when the medium, which surrounds the oscillatory fork, changes. The electronics unit 22 of the field device 2 controls the frequency, with which the oscillatable unit is excited to oscillate and evaluates the received oscillations. For this, there is located in the electronics unit 22 an evaluation unit, which, for example, compares the oscillation frequency with at least one predetermined threshold value and produces for the field device 2 an output signal, which tells whether the threshold value has been achieved or not. The output signal is, for example, a 4-20 mA signal. The electronics unit 22 includes, preferably, at least one microcontroller. A measuring device of the described type is produced and sold by the assignee under the mark "LIQUIPHANT" in a number of embodiments.

The invention will now be explained in greater detail based on this vibronic fill level measuring device. The invention is, however, not limited to such field devices 2, but, instead, is applicable anywhere where communication with the electronics unit 22 of a field device 2 via a contactless interface is desired. Advantageously, the invention is applicable especially also in the case of limit level switches based on the capacitive and/or conductive, measuring principle(s). Such limit level switches are produced and sold by the assignee under the mark "LIQUIPOINT".

Arranged in the interior of the field device housing is a switch element in the form a reed switch 23 actuatable contactlessly from outside of the field device 2. Such switches are well known from the state of the art and have, as a rule, two reeds of ferroelectric material, which, in the resting state, overlap one another, without contacting. Switch 23 is open in the resting state. If this arrangement is placed in a magnetic field, the reeds come together, so that the switch 23 closes. The reed switch 23 is electrically connected with the electronics unit 22 of the field device 2.

In a form of embodiment of the field device 2, the reed switch 23 serves in on-going operation as an activation switch, for example, in order to initiate a test function or a calibration function, whose program is stored in the electronics unit 22. During manufacturing, maintenance or performance of a service task by a service technician, the reed switch 23 functions as a communication interface and enables transmission of field device specific data. For actuating the reed switch 23, there exist then preferably two different apparatuses. For one time actuation of the reed switch 23, for example, a test magnet can serve, which is held against the field device housing. The second apparatus is the illustrated servicing device 1, which enables a modulating of the switch state according to a preselected transmission protocol. The servicing device 1 is, thus, more complex than a simple magnet. Of course, the servicing device 1 can also undertake the function of the test magnet and actuate the reed switch 23 once.

The servicing device 1 is embodied in such a manner that it can communicate with the field device 2 via the reed switch 23 present in the field device 2. For this, the servicing device 1 possesses a field producing unit, which includes a coil 12, a coil core 11 and a power control module 13. Furthermore, an interface to an energy source 5 and an interface to an external electronics unit 15 with means for input of data are present. For distinguishing the electronics unit 22 of the field device 2, this electronics unit is referred to as the second electronics unit 15.

The second electronics unit 15 is, for example, part of a computer. In this case, data can be input via the keyboard 16 of the computer. Alternatively, the second electronics unit 15 can also be embodied as a component of the servicing device 1. The servicing device 1 includes then for input of data for example, a keyboard, input buttons, or a touch screen.

Power control module 13 is connected with an energy source 5 and controls the power of the electrical current, which flows through the windings the coil 12. Furthermore, the power control module 13 is connected with the second electronics unit 15. This controls the power control module 13 corresponding to the data to be transmitted and according to the transmission protocol, which agrees with that of the electronics unit 22 of the field device 2. Coil core 11 is ring-shaped and has a gap, into which the field device 2 and especially its section, in which the reed switch 23 is arranged, are introducible. The magnetic field lines of the magnetic field produced by the coil 12 extend in the region of the gap approximately parallel to one another.

Field device 2 is connected via a connection cable likewise to an energy source 5. The output signal of the field device 2 is fed via the same connection cable to the second electronics unit 15. In this way, field device 2 is enabled to transmit a response to data supplied to it via the reed switch 23, for example, as a check function for the correct transmission of the data.

The servicing device 1 supplies via the reed switch 23, for example, the following parameters into the electronics unit 22 of the fill level measuring device:
  subceeding, or falling beneath, or exceeding of a predetermined fill level);
  switching behavior, for example, whether a covering with foam leads to a covered report or an uncovered report;
  parameters of the switching curve;
  tuning, done at the manufacturer;
electronics unit of the field device.

Furthermore, the servicing device 1 can execute diagnostic functions, such as bringing about test settings of display elements, such as light-emitting diodes 24, or producing a certain output signal.

For data transmission to the field device 2, preferably a protocol is selected that requires little energy. In the ideal case, this means that in the base state no magnetic field is present. In this way, it is simultaneously prevented that through longer lasting applying of the magnetic field the coil core 11 goes into saturation. Another opportunity for preventing saturation is composed in the producing of a magnetic field whose poling alternates.

Figure 2:
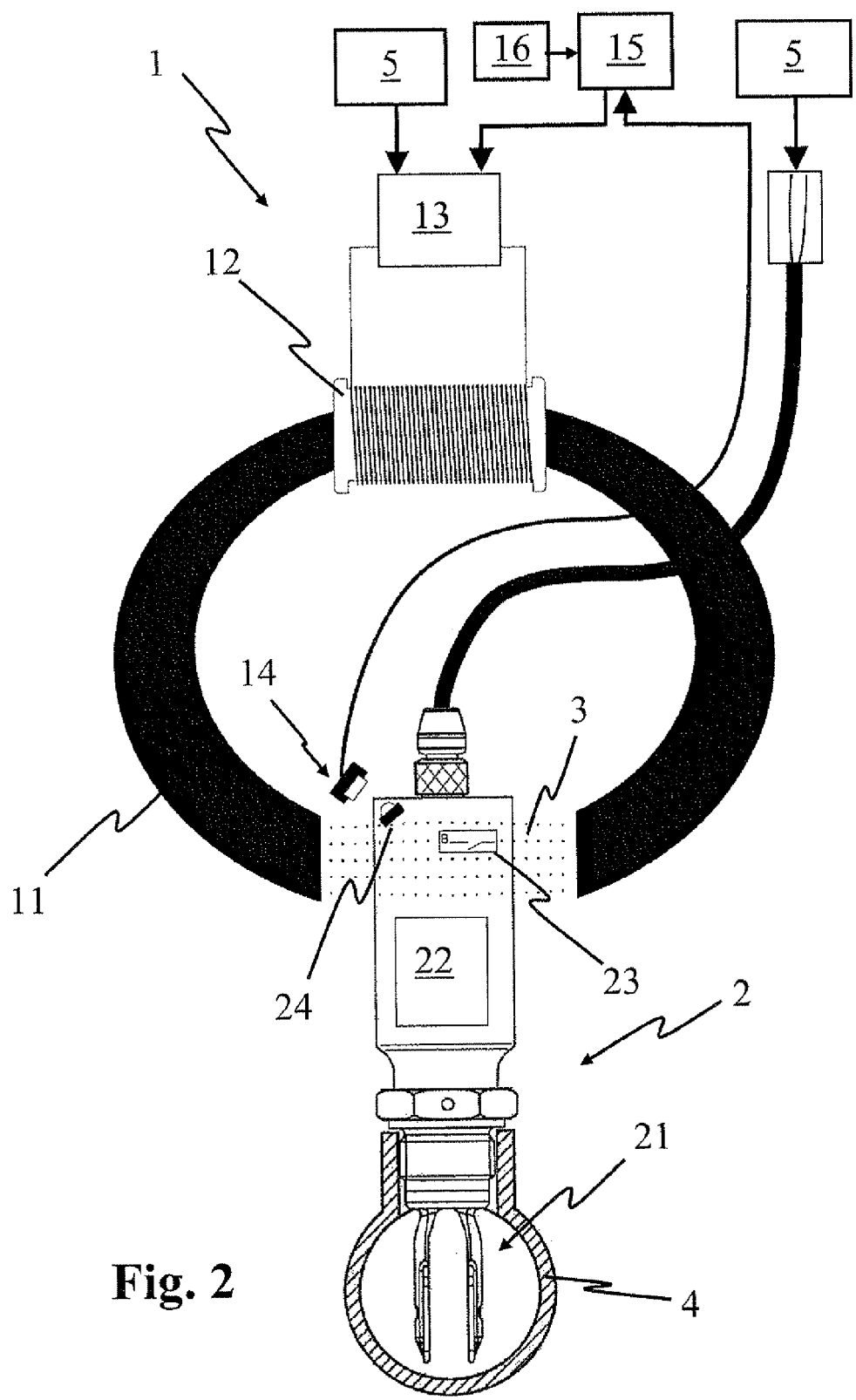
FIG. 2 is a second form of embodiment of a system composed of field device and servicing device.

FIG. 2 shows the field device 2 and the servicing device 1 in a second embodiment. This form of embodiment differs from that illustrated in FIG. 1 as regards the communication response channel.

The response communication from the field device 2 to the servicing device 1, respectively to the external, second electronics unit 15 occurs via an optical interface. For communication outwardly, the electronics unit 22 of the field device 2 controls one or more optical display elements, preferably in the form of light-emitting diodes 24. The servicing device 1 possesses an optical sensor system 14 for registering the optical signals, which are transmitted from the light-emitting diode 24 of the field device 2. Preferably, the optical sensor system 14 is arranged shielded from ambient light, so that the optical signals of the field device 2 are registerable unequivocally and reliably. The servicing device 1 can, for this, also have a housing.

Light-emitting diode 24 can be activated once or according to a protocol and be deactivated and, thus, serve for transmitting data. For example, the electronics unit 22 of the field device 2 turns on a light-emitting diode 24, when a parametering via the reed switch 23 was successfully performed. Furthermore, an option is that the servicing device 1 initiates the performing of a function test, in the case of which the switching function is exercised for test purposes. Light-emitting diode 24 can then signal the switch state.

The servicing device 1 is furthermore embodied to bring about the read-out of certain data from the field device 2, wherein the field device 2 transmits the requested data via the optical interface according to the preselected protocol.

The invention claimed is:
1. A system comprising:
a servicing device;
a field device having at least one sensor unit for determining and/or monitoring at least one process variable; and
at least one electronics unit, which has an evaluation unit, wherein:
said evaluation unit receives measurement signals from said sensor unit and evaluates such with reference to the process variable, and at least one switch element actuatable contactlessly from outside of said field device; and
said servicing device is embodied to modulate the switch state of said switch element for transmission of field device specific parameter data or diagnostic data to said electronics unit, wherein:
said switch element is actuatable from outside of said field device via a magnetic field; and
said servicing device produces a modulatable magnetic field.
2. The system as claimed in claim 1, wherein:
said field device includes at least one optical display element; and
said electronics unit transmits data to said servicing device via said optical display element.
3. A field device for application in a system as claimed in claim 1, wherein:

said field device comprises at least one sensor element for determining and/or monitoring at least one process variable;

at least one electronics unit;

at least one switch element actuatable contactlessly from outside of said field device; and said electronics unit is embodied to receive field device specific parameter data or diagnostic data via said switch element.

4. A servicing device for application in a system as claimed in claim 1, wherein:

said servicing device comprises at least one field producing unit for producing a modulatable magnetic field;

said field producing unit is embodied in such a manner that the magnetic field produced by said field producing unit modulates the switch state of said switch element of said field device.

5. The servicing device as claimed in claim 4, wherein:

said servicing device includes an optical sensor system, which registers optical signals coming from said field device.

6. The servicing device as claimed in claim 4, wherein:

said servicing device has a second electronics unit and means for input of field device specific data or is connectable with a second electronics unit and means for input of field device specific data;

said second electronics unit contains a protocol for transmission of field device specific data to said field device; and said second electronics unit controls said field producing unit in such a manner that said field producing unit produces the magnetic field corresponding to the protocol and to the specific parameter data or diagnostic data to be transmitted.

7. A method for communication between a servicing device and a field device having at least one sensor unit, at least one electronics unit and at least one switch element actuatable contactlessly from outside of the field device, wherein:

for transmission of field device specific data from the servicing device to the electronics unit the switch state of the switch element is modulated.

8. The method as claimed in claim 7, wherein:

the switch state of said switch element is modulated according to a transmission protocol.

9. The method as claimed in claim 7, wherein:

parameter data and/or diagnostic data are transmitted by means of said switch element.

\* \* \* \* \*